United States Patent [19]

Gutteridge et al.

[11] Patent Number: 5,559,156
[45] Date of Patent: Sep. 24, 1996

[54] METHOD FOR TREATING ANIMALS INFECTED WITH BABESIA SPP.

[75] Inventors: Winston E. Gutteridge; Alan T. Hudson; Victoria S. Latter; Mary Pudney, all of Beckenham, England

[73] Assignee: Glaxo Wellcome, Inc., Research Triangle Park, N.C.

[21] Appl. No.: 335,990

[22] Filed: Nov. 8, 1994

Related U.S. Application Data

[63] Continuation of Ser. No. 104,034, filed as PCT/GB92/02344 Dec. 17, 1992.

[51] Int. Cl.$^6$ ................................................ A61K 31/12
[52] U.S. Cl. ................................................ 514/682
[58] Field of Search ................................................ 514/682

[56] References Cited

PUBLICATIONS

Chemical Abstracts, vol. 101, No. 183497, issued 1984, Fry et al, "Potent and Selective hydroxynaphthoquinone inhibitors of Mitochondrial Electron transport in *Emeria tenella* (Apicomphxa: Coccdia)", Biochem. Pharmacol. 33(13), pp. 2115–2122, 1984. Abstract Only.

*Primary Examiner*—Marianne M. Cintins
*Assistant Examiner*—Keith MacMillan
*Attorney, Agent, or Firm*—George W. Neuner

[57] ABSTRACT

The present invention relates to pharmaceutical compositions for the treatment and/or prophylaxis of protozoal infections caused by Kinetoplastida, Apicomplexa, Anaerobic protozoa and Mircosporidia comprising 2-[4-(4-chlorophenyl)cyclohexyl]-3-hydroxy-1,4-naphthoquinone or a physiologically acceptable salt or other functional derivative thereof as active ingredient and to a method of treating or preventing siad protozoal infections in an animal which comprises administering to said animal an effective amount of siad compound.

4 Claims, No Drawings

METHOD FOR TREATING ANIMALS INFECTED WITH BABESIA SPP.

This is a continuation of copending application(s) Ser. No. 08/104,034, filed on Sep. 30, 1993", and a continuation of International Application PCT/GB 92/02344, filed on Dec. 17, 1992, and which designated the U.S."

The present invention relates to the treatment and prophylaxis of protozoal infections caused by Kinetoplastida, Apicomplexa, Anaerobic protozoa and Microsporidia. More particularly the invention is concerned with the use of 2-[4-(4-chlorophenyl)cyclohexyl]-3-hydroxy-1,4-naphthoquinone and physiologically acceptable salts and physiologically functional derivatives thereof in the treatment and prophylaxis of protozoal infections caused by Kinetoplastida, Apicomplexa, Anaerobic protozoa and Microsporidia, and the use of said compound for the manufacture of medicaments for the treatment and prophylaxis of said protozoal infections.

Kinetoplastida include the Trypanosomes of which *Trypanosoma rhodiense, Trypanosoma gambiense* and *Trypanosoma cruzi* are of particular importance. *T. rhodiense* and *T. gambiense* cause sleeping sickness, which is fatal in humans unless treated. The trypanosome parasites live and multiply initially in the blood and tissue fluid of their host, producing a febrile condition which may be quite mild. After a few months (*T. rhodiense*) or a year or so (*T. gambiense*) the parasites invade the central nervous system and multiply in the cerebrospinal fluid, ultimately causing brain damage which leads to the coma from which the disease gets its name.

*T. cruzi* causes Chagas disease in humans. In children, the disease takes the form of an acute fever which can cause death. In adults, the infection is chronic, involves the heart or the alimentary tract and can be fatal.

The Kinetoplastida also include the genus Leishmania which cause leishmaniasis in humans. The parasites are also frequently found in dogs and rodents which may serve as reservoirs for the parasite. Leishamania parasites are ingested by the macrophage cells of their host, but instead of being destroyed the parasites thrive and multiply within the macrophages. In visceral leishmaniasis, caused by *L. donovani*, parasitized macrophages occur in all tissues, including the blood, and although the disease is slow, it is usually fatal unless treated. *L. tropica* causes cutaneous leishmaniasis in which the parasites are restricted to ulcers in the skin. In Brazil, *L-Braziliensis* causes mucocutaneous leishmaniasis which is a very severe disease; the mucous membranes of the nose, mouth and pharynx become infected and ultimately destroyed.

The Apicomplexa include the Babesia parasites which inhabit erythrocytes and which are of veterinary as well as medical importance. *B. divergens* is the European species that causes bovine babesiosis and, although not normally parasitic in man, it can cause a life threatening disease in splenectomized individuals, for which there is not recommended chemotherapy. The disease is usually associated with anaemia, fever, enlargement of the spleen and blocking of the capillaries in various tissues (including the brain), which may damage the cells by depleting their oxygen supply. The anaemia may be accompanied by the lysis of erythrocytes and excretion of the released haemoglobin in the urine.

The Isospora are a genus of Apicomplexa which may infect humans and cause diarrhoea. Another genus of Apicomplexa which may infect humans are the Sarcocystis which commonly infect herbivores. All species of Sarcocystis are almost entirely restricted to the muscle fibres of their host. If the infection is heavy, degeneration of the surrounding muscle fibres and consequent muscular weakness results along with some pain.

Parasitic anaerobic protozoa include species of Acanthanamoeba which normally inhabit soil and a mud but which can cause throat infections in humans, particularly in infants.

*Entamoeba histolytica* is an anaerobic protozoan which normally inhabits the gut as a harmless commensal Occasionally however, the parasites penetrate the mucosa and invade the sub-mucosa where they multiply to form a flask-shaped lesion or ulcer. Secondary bacterial infection of the ulcer may also occur. As the submucosa is eroded, many blood vessels are broken and bloody dysentery results. A common complication is the spread of amoebae via blood vessels to other organs, where they invade and destroy the organ tissue and cause amoebic abscesses. The commonest site for development of such abscesses is the liver, because most of the blood from the gut is carried there by the hepatic portal system. Untreated amoebic dysentery may result in death from fluid and blood loss.

*Giardia lamblia* is a species of anaerobic protozoa which inhabits the small intestine of humans, monkeys and pigs. It is common in humans, especially in children, and can cause a disease called giardiasis or lambliasis. Heavy infections may cause acute diarrhoea and epigastric pain. The parasites are through sometimes to swim up the bile duct into the gall bladder where they may produce symptoms of jaundice, nausea and vomiting.

*Trichomonas vaginalis* is an anaerobic protozoan which inhabits the female vagina and the male urethra or prostrate and is common throughout the world, particularly in women. Most commonly, the parasite is non-pathogenic. However, the organism may be responsible for vaginal inflammation associated with a discharge in women and, more rarely, for inflammation of the urethra in males.

Infection by Microsporidia, such as *Enterocytozoon bieneuisi* or *Encephalitozoon cuniculi* causes an increase in the size of infected cells to such an extent that those cells cannot perform their natural function.

Encephalitozoon cuniculi can cause an encephalitis in humans in which the parasites are present in the cerebrospinal fluid.

Patients in an already weakened state, such as children and the elderly, are particularly vulnerable to protozoal infections caused by Kinetoplastida, Apicomplexa, Anaerobic protozoa and Microsporidia. Such protozoal infections can also be an extremely debilitating and complicating factor in immunocompromised patients (i.e. those with a defective or deficient immune system), who may be suffering from a number of different infections. There is a variety of circumstances in which the immune system may be defective or deficient. Thus, for example immune system deficiency is common in immature or premature infants (neonates). It may also result from suppression by certain drugs, which may be deliberate e.g. in certain patients receiving organ transplants, or unavoidable e.g. as a side-effect of cancer chemotherapy. Disordered growth of one or more constituent parts of the immune system, e.g. as in certain forms of cancer, may also result in immunodeficiency. Immune deficiency may furthermore be caused by viral infections, including human immunodeficiency virus (HIV).

Treatment of protozoal infections caused by Apicomplexa, Kinetoplastida, Anaerobic protozoa and Microsporidia is generally concerned with alleviating the symptoms rather than combatting the causative organism. There is thus a need for chemotherapeutic agents to combat the said protozoal infections.

The compound 2-[4-(4-chlorophenyl)cyclohexyl]-3-hydroxy-1,4-napthoquinone has previously been disclosed, for example in European Patent No. 123,238 which related to 2-substituted-3-hydroxy-1,4-naphthoquinones of formula (I)

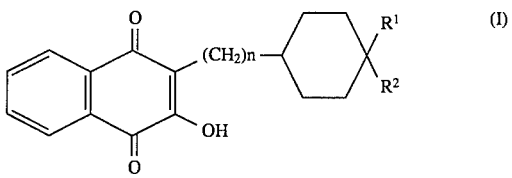

wherein either $R^1$ is hydrogen and $R^2$ is selected from $C_{1-6}$ alkoxy, aralkoxy, $C_{1-6}$ alkyl-$C_{1-6}$ alkoxy, phenyl substituted by one or two groups selected from halogen ad $C_{1-6}$ alkyl, halogen and perhalo-$C_{1-6}$ alkyl or $R^1$ and $R^2$ are both $C_{1-6}$ alkyl or phenyl, and n is zero or 1, and physiologically acceptable salts thereof. The compounds are said to have antiprotozoal activity. Specifically, compounds of formula (I) wherein n is zero are said to be active against the human malaria parasite *Plasmodium falciparum* and also against Eimeria species such as *E. tenella* and *E. acervulina*, which are causative organisms of coccidiosis and compounds of formula (I) where n is 1 are said to be active against protozoa of the genus Theileria, in particular *T. annulata* or *T. parva*. Amongst the compounds specifically named and exemplified is the compound of formula (I) wherein n is zero, $R^1$ is hydrogen and $R^2$ is 4-chlorophenyl, i.e. 2-[4(4-(4-chlorophenyl)cyclohexyl]-3hydroxy-1,4-naphthoquinone.

It has now surprisingly been found that 2-[4(4-chlorophenyl)cyclohexyl]-3hydroxy-1,4-naphthoquinone, represented in this specification by formula (II):

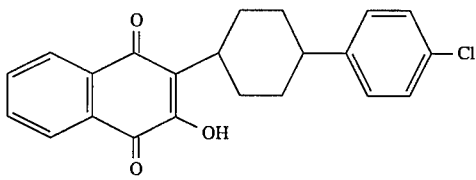

exhibits activity against protozoal infections caused by Kinetoplastida, Apicomplexa, Anaerobic protozoa and Microsporidia.

Thus, in a first aspect the present invention provides the compound of formula (II) and physiologically acceptable slats and other physiologically functional derivatives thereof for use in the treatment and/or prophylaxis of protozoal infections caused by Kinetoplastida, Apicomplexa, Anaerobic protozoa and Microsporidia in mammals (including humans).

In another aspect the present invention provides the use of the compound of formula (II) and physiologically acceptable salts and other physiologically functional derivatives thereof for the manufacture of a medicament for the treatment and/or prophylaxis of protozoal infections caused by Kinetoplastida, Apicomplexa, Anaerobic protozoa and Microsporidia in mammals (including humans).

According to a further aspect the present invention provides a method of treating and/or preventing protozoal infections caused by Kinetoplastida, Apicomplexa, Anaerobic protozoa and Microsporidia which comprises administering to mammal (including a human) suffering from or susceptible to infection with said protozoa an effective amount of a compound of formula (II), or a physiologically acceptable salt or other physiologically functional derivatives thereof.

Prevention of protozoal infections is particularly important in an immunocompromised host, as discussed hereinabove. In the case of immunosuppression resulting from HIV infection, prophylaxis may be required by those diagnosed as seropositive for HIV (i.e. having antibodies to HIV) and those with progressive generalised lymphadenopathy (PGL) or AIDS-related complex (ARC) as well as patients suffering from AIDS.

The hydroxyl group in the compound of formula (II) may form slats with appropriate bases, and physiologically acceptable salts of the compound (II) include inorganic base slats such as alkali metal (e.g. sodium and potassium) salts and alkaline earth metal (e.g. calcium salts; organic base slats e.g. phenylethylbenzylamine, dibenzylethyl-enediamine, ethanolamine and diethanolamine salts; and amino acid salts e.g. lysine and arginine.

Physiologically functional derivatives of formula (II) are derivatives which are converted in vivo, either by the host or the parasite to a compound of formula (II). Such derivatives include those of formula (III):

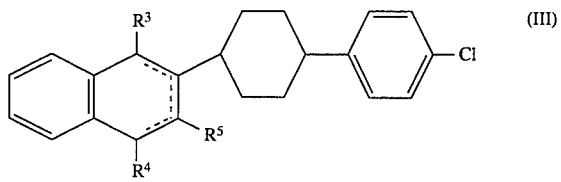

wherein $R^3$ and $R^4$ each represent —O and the dotted line represents a double bond between the 2 and 3 positions of the quinone ring, in which case $R^5$ represents a group —OCOR$^6$, wherein $R^6$ is a $C_{1-10}$ alkyl group, a $C_{3-10}$cycloalkyl group, a $C_{1-10}$ alkoxy group, or a phenyl or naphthyl group, each such $R^6$ group being optionally substituted e.g. by amino, mono- or di-$C_{1-4}$ alkylamino, carboxy or hydroxy; a group OR$^7$ or SR$^7$, wherein $R^7$ is an optionally substituted $C_{1-10}$ alkyl, $C_{3-10}$ cycloalkyl, phenyl or naphthyl group as defined for $R^6$; or a group NR$^8$R$^9$, wherein $R^8$ and $R^9$ each independently represent hydrogen or $C_{1-4}$ alkyl, or the group NR$^7$R$^8$ represents a 5–7 membered saturated heterocyclic ring, which may optionally contain a further heteroatom selected from bitrogen, oxygen or sulphur; or the dotted line represents double bonds at the 1,2 and 3,4 positions of the quinol ring and $R^3$, $R^4$ and $R^5$ each represents a group —OCOR$^{10}$, wherein $R^{10}$ represents an optionally substituted $C_{1-10}$alkyl group.

It will be appreciated that the compound of formula (II) may exist as the cis or trans iosomer, that is to say that the cyclohexyl ring may be cis or trans substituted by the naphthoquinone nucleus and the chlorophenyl group. Both cis and trans isomers and mixtures thereof in any ratio may be used in accordance with the present invention. In general when the compound is in the form of a mixture of isomers the trans isomer will be present in an amount of about 50% or will be the predominant isomer but the use of mixtures in which the cis isomer predominates is also included within the scope of the invention. The specific ratio of isomers may be varied as required: typical mixtures include those in which the cis/trans isomer ratio is about 1:1,40:60 and 5.95. For use according to the present invention the trans isomer of the compound of formula (II), or a mixture of its cis and trans isomers containing at least 95% e.g. 99% of the trans isomer, is preferred.

The compound of formula (II) may also exist in a tautomeric form in which the hydroxyl group donates its proton to one of the oxo groups and the use of such tautomeric forms is included within the scope of this invention. However, it is believed that the stable form is that shown in formula (II).

It will be appreciated that the amount of a compound of formula (II) or its salt or other physiologically functional derivative required for use in the treatment or prophylaxis of protozoal infections caused by Kinetoplastida, Apicomplexa, Anaerobic protozoa and Microsporidia will depend inter alia on the route of administration, the age and weight of the mammal (e.g. human) to be treated and the severity of the condition being treated. In general, a suitable dose for administration to man for the treatment of protozoal infections caused by Kinetoplastida, Apicomplexa, Anaerobic protozoa and Microsporidia is in the range of 1.0 mg to 200 mg per kilogram bodyweight per day, for example from 5 mg/kg to 100 mg/kg, particularly 25 to 100 mg/kg. It will be appreciated that for administration to neonates, lower doses may be required.

For prophylactic treatment the compound of formula (II) or a physiologically acceptable salt or other physiologically functional derivative thereof may also be given less frequently, e.g. as a single dose on alternate days, once or twice per week or once or twice per month. The dosage for prophylactic treatment will depend inter alia on the frequency of administration, and, where a depot preparation or controlled release formulation is used the rate of release of the active ingredient. Thus for once-weekly administration a suitable prophylactic dose is in the range 0.5 to 100 mg/kg, e.g. 1.0 to 50 mg/kg particularly 5 to 50 mg/kg.

It should be understood that the dosages referred to above are calculated in terms of the compound of formula (II) per se.

For use according to the present invention the compound of formula (II) or a physiologically acceptable salt or other physiologically functional derivative thereof is preferably presented as a pharmaceutical formulation.

Pharmaceutical formulations comprise the active ingredient (that is, the compound of formula (II) or a physiologically acceptable salt or other physiologically functional derivative thereof) together with one or more pharmaceutically acceptable carriers thereof and optionally other therapeutic and/or prophylactic ingredients. The carrier(s) must be acceptable in the sense of being compatible with the other ingredients of the formula and not deleterious to the recipient thereof.

The compound of formula (II) or its salt or other physiologically functional derivative may conveniently be present as a pharmaceutical formulation in unit dosage form. A convenient unit dose formulation contains the active ingredient in an amount of from 10 mg to 3 g, e.g. 50 mg to 3 g. A typical unit dose may contain for example 50 mg, 1 g, 2 g or 3 g of the active ingredient.

Pharmaceutical formulations include those suitable for oral, topical (including dermal, buccal and sublingual), rectal and parenteral (including subcutaneous, intradermal, intramuscular and intravenous), administration as well as administration by naso-gastric tube. The formulation may, where appropriate, be conveniently presented in discrete dosage units and may be prepared by any of the methods well known in the art of pharmacy. All methods include the step of bringing into association the active ingredient with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of the active ingredient. A tablet may be made by compression or moulding, optionally with one or more accessory ingredients. Compressed tablets may be prepared by compressing in a suitable machine the active compound in a free-flowing form such as a powder or granules optionally mixed with a binder, lubricant, inert diluent, lubricating agent, surface-active agent or dispersing agent. Moulded tablets may be made by moulding an inert liquid diluent. Tablets may be optionally coated and, if uncoated, may optionally be scored. Capsules may be prepared by filling the active ingredient, either alone or in admixture with one or more accessory ingredients, into the capsule shells and then sealing them in the usual manner. Cachets are analogous to capsules wherein the active ingredient together with any accessory ingredient(s) is sealed in a rice paper envelope. The compound of formula (II) or a physiologically acceptable slat or other physiologically functional derivative thereof may also be formulated as dispersible granules, which may for example be suspended in water before administration, or sprinkled on food. The granules may be packaged e.g. In a sachet. Formulations suitable for oral administration wherein the carrier is a liquid may be presented as a solution or a suspension in an aqueous liquid or a non-aqueous liquid, or as an oil-in-water liquid emulsion.

Formulations for oral administration include controlled release dosage forms e.g. tablets wherein the active ingredient is formulated in an appropriate release—controlling matrix, or is coated with a suitable release—controlling film. Such formulations may be particularly convenient for prophylactic use.

The active ingredient may also be formulated as a solution or suspension suitable for administration via a naso-gastric tube.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active compound with the softened or melted carrier(s) followed by chilling and shaping in moulds.

Pharmaceutical formulations suitable for parenteral administration include sterile solutions or suspensions of the active compound in aqueous or oleaginous vehicles. Injectible preparations may be adapted for bolus injection or continuous infusion. Such preparations are conveniently presented in unit dose or multi-dose containers which are sealed after introduction of the formulation until required for use. Alternatively, the active ingredient may be in powder form which is constituted with a suitable vehicle, such as sterile, pyrogen-free water, before use.

The compound of formula (II) or a physiologically acceptable salt or other physiologically functional derivative thereof may also be formulated as a long-acting depot preparation, which may be administered by intramuscular injection or by implantation e.g. subcutaneously or intramuscularly. Depot preparations may include, for example, suitable polymeric or hydrophobic materials, or ion-exchange resins. Such long-acting formulations are particularly convenient for prophylactic use.

It should be understood that in addition to the aforementioned carrier ingredients the pharmaceutical formulations for the various routes of administration described above may include, as appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

The compound of formula (II) or a physiologically acceptable salt or other physiologically functional derivative thereof may also be used in accordance with the present invention in combination or concurrently with other therapeutic agents, for example agents used the treatment of immunocompromised patients, including antibacterial agents; antifungal agents; anticancer agents such as interferon e.g. alpha-interferon; antiviral agents such as azidothymidine (AZT, zidovudine); immunostimulants and immunodulators. The compound of formula (II) may also be administered in combination with a 4-pyridinol compound, as described in EPA 123,239 e.g. 3,5-dichloro-2,6-dimethylpyridinol (meticlorpindol). The compound of formula (II) may also be administered in combination or concurrently with anti-diarrhoeal agents such as loperamide hydrochloride and/or diphenoxylate hydrochloride, or with morphine sulphate. Oral rehydration therapy may also be carried out concurrently.

Compositions suitable for veterinary use include those adapted for oral, parenteral, and intrarumenal administration.

Compounds suitable for oral administration include drenches (oral liquid dosing), which may be solutions or suspensions; tablets, boluses, pastes, or in-feed preparations in the form of powders, granules or pellets.

Alternatively, veterinary compositions may be adapted to be administered parenterally by sub-cutaneous, intramuscular or intravenous injection of a sterile solution or suspension, by implantation or as an intramammary injection whereby a suspension or solution is introduced into the udder via the teat.

For intrarumenal injection, the compositions of the invention may be solutions or solid or microcapusule suspensions. Typically the compositions are similar to the oral liquid preparations or parenteral preparations described herein. Such compositions are injected directly into the rumen, usually through the side of the animal, for example by a hypodermic syringe and needle or by an automatic injection device capable of giving single or multiple doses.

For veterinary administration the compound of formula (II) or its salt or other physiologically functional derivative is preferably formulated with one or more veterinarily acceptable carriers.

For oral administration, fine powders or granules may contain diluting agents, for example lactose, calcium carbonate, calcium phosphate, mineral carriers, etc., dispersing and/or surface active agents, for example polysorbates such as Tweens or Spans, and may be presented in a drench, in water or in a syrup, in a bolus, paste, or in a feed preparation, in capsules or sachets in the dry state or in a non-aqueous suspension, or in a suspension in water or syrup. Where desirable or necessary, preserving, suspending, thickening or emulsifying agents can be included. If intended for oral use, a bolus will be provided with retention means to inhibit regurgitation, for example it may be weighted with a heavy density material such as iron or tungsten or the like or may be retained by its shape, for example by wings which spring after administration. Boluses may contain disintegrating agents such as maize starch or calcium or sodium methyl celluloses, hydroxypropylmethylcellulose, guar based vegetable gums, sodium alginates or sodium starch glycolates; granulating or biding agents such as starch in the form of mucilage, starch derivatives, such as "Snow Flake", cellulose derivatives such as talc, calcium stearate, methyl cellulose, gelatin or polyvinylpyrrolidone; and/or lubricating agents, such as magnesium stearate or stearic acid.

For parenteral administration, the compounds may be presented in sterile injection solutions which may contian antioxidants or buffers, or as injectable suspensions. Suitable solvents include water, in the case of suspensions, and organic solvents such as dimethylformamide, dimethylacetamide, diethylacetamide, ethyl lactate, ethyl akate, dimethylsulphoxide, alchols, e.g. ethanol, glycols, e.g. ethylene glycol, propylene glycol, butylene glycol and hexamethylene glycol, polyethylene glycols containing 2 to 159 ethylene glycol monomer units and having average molecular weights from about 90 to 7500, glycerin formal, glycofural, glycerol, isopropylmyristate N-methylpyrrolidone, 2-pyrrolidone polyethylene glycoethers or tetrahydrofurfuryl alcohol and diethylene glycol, and fixed and neutral oils, for example fractionated coconut oil. Parenteral formulations may also contain isotonic agents.

For veterinary use the compound of formula (II) may be employed together with other therapeutic agents used in the field of animal health, for example with anticoccidial and/or antitheilerial agents.

Methods for preparing the compound of formula (II) are described in EP 123,238, and one specific method is illustrated in Example 1.

EXAMPLE 1

2-[trans-4-(4-Chlorophenyl)cyclohexyl]-3-hydroxy-1,4-naphthoquinone a) 4-(4-Chlorophenyl)cyclohexane-1-carboxylic Acid

Acetyl chloride (30 g) and finely powdered aluminium chloride (60 g) were stirred together in carbon disulphide (120 ml) and then cooled to 31 50° C., in a $CO_2$/oxitol bath. Cyclohexene (30 g), previously cooled to −50° C., was added dropwise during 10 minutes while maintaining the temperature of the reaction mixture at below −20° C. The mixture was stirred at −50° C. for a further 60 minutes and the solvent then decanted to leave a gummy orange complex. A little chlorobenzene was added as the material warmed to ambient temperature; the remainder of the chlorobenzene (total 300 ml) was then added, the so-obtained solution heated at 40° C. for 3 hours with stirring, poured onto a mixture of ice and concentrated hydrochloric acid and the organic layer separated, washed with 2M hydrochloric acid, 2M sodium hydroxide and water, dried over anhydrous sodium sulphate and evaporated to dryness. The product was distilled in vacuo, the fraction boiling at 140°–154° C. (0.1 mm Hg) collected, diluted with an equal volume of petroleum ether (40-60), cooled to −6° C. and a continuous stream of nitrogen gas bubbled through, and the separated colourless solid recovered.

Bromine (2.8 ml) was added to a solution of sodium hydroxide (6.2 g) in water (42 ml) at 0° C. The above-obtained substituted hexahydroacetophenone (3.1 g) was dissolved in dioxan (15 ml) and the cold hypobromite solution then added, keeping the reaction mixture at below 20° C. The reaction mixture was stirred at ambient temperature for 6 hours then allowed to stand overnight. Sodium metabisulphite was added to destroy excess hypobromite, the mixture cooled and then acidified to give a colourless solid. The solid was filtered off, washed with water, dried and recrystallised from ethanol to give 4-(4-chlorophenyl)cyclohexane-1-carboxylic acid, m.p. 254°–256° C.

b) 2-[4-(4-chlorophenyl)cyclohexyl]-3-chloro-1,4-naphthoquinone

A mixture of 2-chloro-1,4-naphthoquinone (3.95 g, 0.02 mol), 4-(4-chlorophenyl)cyclohexane-1-carboxylic acid (4.9 g, 0.02 mol) and powdered silver nitrate (1.05 g, 0.0062 mol) was heated to reflux with vigorous stirring in 40 ml of acetonitrile. A solution of ammonium persulphate (12.0 g, 0.0525 mol) in 50 ml of water was added dropwise over 1 hour. The mixture was refluxed for 3 hours then cooled in ice for 30 mins, after which it was filtered, and the residual sticky solid extracted twice with boiling chloroform to remove inorganic material. The chloroform was removed by evaporation to leave a yellow-brown solid (ca 2.7 g). This was dissolved in 40 ml of boiling acetonitrile; a little insoluble material was removed by filtration. On cooling, the title compound separated as yellow crystals, (550 mg) m.p. 172°–175° C.

NMR, $\delta H(d_6\text{-DMSO})$ 8.05 (2H, mult., β-naphth), 7.85(2H, mult., α-naphth), 7.30 (4H, s., PhH), 3.30 (1H, br.t., CH), 2.67 (1H, br.t., CH), 1.2–2.4 (8H, mult., 4×CH$_2$).

c) 2-[4(4-chlorophenyl)cyclohexyl]-3-hydroxy-1,4-naphthoquinone

The product of state (b) was suspended in 10 ml of boiling methanol and 0.55 g of potassium hydroxide in 5.5 ml of water was added dropwise over 15 mins. The mixture was refluxed until a dark red solution formed, (after ca. 6 hrs) when 2 ml of concentrated hydrochloric acid was cautiously added dropwise. The mixture was cooled and filtered, and the solid residue washed thoroughly with water. The water washings were re-acidified and filtered. The combined solid residues (500 mg) mp 200°–209°, were recrystallised from acetonitrile to give the title product as the trans-isomer (300 mg) m.p. 216°–219° C.

EXAMPLE 2

The following examples illustrate, with reference to the compound of formula (II) per se, pharmaceutical and veterinary formulations which may be employed in accordance with the present invention:

A. Injectable solution

A solution for intramuscular injection may be prepared by mixing:

| | |
|---|---|
| Compound of formula (II) | 9.5 parts by weight |
| Dimethyl sulphoxide | 19.0 parts by weight |
| Sorbitan monooleate | 4.5 parts by weight |
| Corn oil | 67.0 parts by weight |
| | 100.0 |

B. Injectable solution

The following injectable formulation was prepared:

| | |
|---|---|
| Compound of formula (II) | 5 parts by weight |
| N-methyl-pyrollidone | 48.3 parts by weight |
| Tween 80 | 2 parts by weight |
| Span 80 | 4.7 parts by weight |
| Miglyol 812 | 40 parts by weight |
| | 100.0 |

C. Tablet

| | |
|---|---|
| Compound of formula (II) | 25.0 mg |
| Lactose BP | 48.5 mg |
| Microcrystalline Cellulose BP ("Avicel pH 101") | 10.0 mg |
| Low-substituted Hydroxypropyl; Cellulose BP ("LHPC LH-11") | 10.0 mg |
| Sodium Starch Glycollate BP ("Explotab") | 3.0 mg |
| Povidone BP ("K30") | 3.0 mg |
| Magnesium Stearate BP | 0.5 mg |
| | 100.0 mg |

D. Oral suspension

| | |
|---|---|
| Compound of formula (II) | 50 mg |
| Avicel RC 591 | 75 mg |
| Sucrose syrup | 3.5 ml |
| Methylhydroxybenzoate | 5 mg |
| Colour | 0.01% w/v |
| Cherry flavour | 0.1% v/v |
| Tween 80 | 0.2% v/v |
| Water | to 5 ml |

E. Injectable suspension

| | |
|---|---|
| Compound of formula (II) | 100 mg |
| Polyvinyl pyrrolidone (PVP) | 170 mg |
| Tween 80 | 0.2% v/v |
| Methylhydroxybenzoate | 0.1% w/v |
| Water for Injection | to 3 ml |

F. Capsule

| | |
|---|---|
| Compound of formula (II) | 100 mg |
| Starch 1500 | 150 mg |
| Magnesium stearate | 2.5 mg |
| filled into a hard gelatin capsule | |

G. Aqueous Suspension

An aqueous suspension may be prepared as follows:-

| | |
|---|---|
| Compound of formula (II) | 1.00 part by weight |
| Neosyl | 16.00 parts by weight |
| Bentonite | 3.20 parts by weight |
| Glycerin | 15.00 parts by weight |
| Sodium benzoate | 1.00 part by weight |
| Bevaloid 35/2 | 1.00 part by weight |
| Thymol | 0.04 parts by weight |
| Water | 62.76 parts by weight |
| | 100.00 |

H. Salt Block

A salt block may be prepared by mixing a finely divided compound of formula (II) (0.5 parts by weight) with sodium chloride (99.5 parts by weight) and the mixture pressed into blocks.

I. Paste

The following paste may be prepared:

| | |
|---|---|
| Compound of formula (II) | 3.0 parts by weight |
| Gum tragacanth | 4.0 parts by weight |
| Bevaloid 35/3 | 1.0 part by weight |
| Nipagin "M" | 0.1 parts by weight |
| Glycerin | 19.0 parts by weight |
| Water | 72.9 parts by weight |
| | 100.00 |

The use of the compound of formula (II) according to the present invention is illustrated by the following example:

BIOLOGICAL TEST RESULTS

EXAMPLE 3

Activity against Babesiosis in vitro
Test Compound
A: 2-[trans-4-(4-chlorophenyl)cyclohexyl]-3-hydroxy-1,4-naphthoquinone
Method The activity of the test compound against B-divergens in vitro, both in bovine and human red cells was measured and compared with the activities of standard anti-babesials.

The results, which are presented in Table 1 below, indicate that the test compound was active at $10^{-8}$ M levels in human cells against *B-divergens*. *B-divergens* is the European species of bovine babesiosis which can cause life threatening disease in splenectomized individuals and for which there is no recommended chemotherapy. However, Imizol has been used successfully in two patients to cure B-divergens and the results show that the test compound is more effective than Imizol in vitro.

TABLE 1

| Compound | $IC_{50}$ M Bovine | Human |
|---|---|---|
| Quinuronium sulphate | $3.4 \times 10^{-8}$ | $9.6 \times 10^{-8}$ |
| Ethidium bromide | $4.7 \times 10^{-8}$ | $6.9 \times 10^{-8}$ |
| Imizol | $1.0 \times 10^{-7}$ | $3.1 \times 10^{-7}$ |
| Pentamidine isethionate | $3.6 \times 10^{-7}$ | $4.56 \times 10^{-7}$ |
| Amicarbalide isethionate | $4.6 \times 10^{-7}$ | $5.17 \times 10^{-7}$ |
| Test compound | $1.79 \times 10^{-8}$ | $3.63 \times 10^{-8}$ |

EXAMPLE 4

Activity against Babesiosis in vitro
Test Compound
2-[4-(4-chlorophenyl)cyclohexyl]-3-hydroxy-1,4-napthoquinone.

Gerbils, in groups of 5, were injected intraperitoneally with gerbil erythrocytes infected with $10^7$ B divergens. At the time of infection, the gerbils were given, per os by stomach tube, a single dose of test compound, diluted in methyl cellulose. The gerbils were assessed for the time to reach 0.1% parasitaemia and the time to reach haemoglobinurea (redwater). The maximum parasitaemia reached and suppression of parasitaemia relative to controls were assessed and the activity of the test compound calculated.

The results which are presented in Table 2 below, indicated that the test compound was active in vivo against *B. divergens* in gerbils.

EXAMPLE 5

Activity against *Leishmania donovani* in vitro
Test Compound
2-[4-(4-chlorophenyl)cyclohexyl]-3-hydroxy-1,4-naphthoquinone; 1:1 mixture of cis and trans isomers.
Method

*Leishmania donovani* was routinely maintained in male golden hamsters (Wright'strain). Amastigotes were isolated from the spleen of infected hamsters 6–8 weeks after infection for use in experimental studies.

The procedure of Neal and Croft (Journal of Antimicrobial Chemotherapy 14, 463–475 (1984) was followed. Mouse peritoneal macrophages were isolated from the peritoneal cavity of outbred CD1 mice. Macrophages were cultured in Labtek eight-well tissue chamber slides in RPMI 1640 medium plus 10% heat-inactivated foetal calf serum at 37° in a 5% $CO_2$-air mixture. Cultures were infected with freshly isolated amastigotes 24 hours before the start of drug treatment. Finally, infected macrophages where incubated in the presence of medium containing the test compound for 7 days, medium being replaced on days 1, 3 and 5 after infection.

The compound was tested in a five-fold dilution series from 50 μM with four replicates at each dilution. Fine suspensions of the compound for testing were prepared by dilution with medium of solutions initially prepared in echanol.

The proportion of infected macrophages in Giemsa stained preparations was determined after 7 days exposure to the test compound. The $ED_{50}$ value was calculated by a sigmoidal analysis.

The results, which are presented in Table 3 below, indicated that the test compound was active at 50 μM concentration against *L. donovani*.

TABLE 3

| Concentration (μM) | % Inhibition |
|---|---|
| 50 | 64.8 |
| 10 | 14.7 |
| 2 | 0 |
| 0.4 | 6 |
| $ED_{50}$ (μM) [P95% limits] | 29.49 [173.14–10.95] |

EXAMPLE 6

Activity against *L. donovani* in vivo
Test Compound
2-[4-(4-chlorophenyl)cyclohexyl]-3-hydroxy-1,4-, naphthoquinone; 1:1 mixture of cis and trans isomers.

TABLE 2

| Drug dose (mg/kg) | Days to 0.1% Parasitaemia | Days to Redwater | Maximum % Parasittaemia | % Control % Parasittaemia (day 3) | % Activity |
|---|---|---|---|---|---|
| 0.00 | 1.0 ± 0.0 | 3.0 ± 00 | >40 | 100 | 0.0 |
| 0.1 | 1.0 ± 0.0 | 3.0 ± 0.0 | >40 | 138.7 ± 18.6 | 0.0 |
| 1.0 | 2.5 ± 0.57 | 4.0 ± 0.82 | >40 | 13.9 ± 4.3 | 86.1 |
| 10.0 | 5.6 ± 2.5 | 9.2 ± 1.8 | 4.02 | 0.0 | 100 |
| 50.0 | >10.0 | >10.0 | 0.0 | 0.0 | 100 |

Method

Male Balb/c mice were infected intravenously with $5\times 10^6$ *L. donovani* amastigotes obtained as in Example 5. One week after infection mice were randomly divided into groups of 5 and treatment with test compound commenced, using cellacol as the vehicle for the test compound. Four days after the completion of treatment all mice were sacrificed. Their livers were removed, weighted and impression smears were fixed with methanol and Giamsa stained. The activity of the compound was determined from the number of amastigotes/500 liver cells in treated and untreated groups.

The results, presented in table 4 below, indicated that the test compound was active when administered subcutaneously.

TABLE 4

| Formulation | Dose | Administration | % Suppresion of Liver Amastigotes |
|---|---|---|---|
| 0.25% cellacol | 100 mg/kg/day × 5 | Oral | 0 |
| 0.25% cellacol | 100 mg/kg/day × 5 | Subcutaneous | 30.5 |

We claim:

1. A method of treating an animal having an infection caused by Babesia spp which comprises administering to said infected animal an effective Babesia spp treatment amount of 2-[4-(4-chlorophenyl) cyclohexyl]-3-hydroxy-1,4-naphthoquinone or a physiologically acceptable salt thereof.

2. A method according to claim 1 where the compound 2-[trans- 4-(4-chlorophenyl)cyclohexyl]-3-hydroxy-1,4-naphthoquinone is administered.

3. A method according to claim 2 wherein the compound or a physiologically acceptable salt thereof is administered in an amount of from 25 to 100 mg per kilogram of animal bodyweight per day.

4. A method according to claim 1 or 2 wherein the animal is a human.

* * * * *